US00PP08340P

United States Patent [19]

Verhoeven

[11] Patent Number: Plant 8,340

[45] Date of Patent: Aug. 10, 1993

[54] IMPATIENS PLANT NAMED BLACKBERRY ICE

[75] Inventor: Thomas A. Verhoeven, Albany, Oreg.

[73] Assignee: Douglas S. Cole, Concord, N.H.

[21] Appl. No.: 765,945

[22] Filed: Sep. 26, 1991

[51] Int. Cl.[5] ..... A01H 5/00

[52] U.S. Cl. ..... Plt./87.6

[58] Field of Search ..... Plt./87.6, 68

[56] References Cited

PUBLICATIONS

Thompson & Morgan Seed Catalog, 1987. p. 100. P.O. Box 1308, Jackson, New Jersey 08527. Phone: (201)363-2225.

*Primary Examiner*—James R. Feyrer
*Assistant Examiner*—Erich Veitenheimer
*Attorney, Agent, or Firm*—Foley & Lardner

[57] ABSTRACT

A new cultivar of *Impatiens sultanii* plant named Blackberry Ice, characterized by its red-purple flower color, its fully double consistent flowers, and its variegated foliage, with the light yellow variegation variably extending from the edge toward the leaf midrib.

1 Drawing Sheet

The present invention comprises a new and distinctive cultivar of Impatiens plant, botanically known as *Impatiens sultanii,* and known by the cultivar name Blackberry Ice. The species name appears to be synonymous with the species designation *Impatiens wallerana,* also referred to in botanical literature.

The new cultivar is a sport or mutation of the cultivar Rosebud TM Purple, and was discovered by the inventor Thomas A. Verhoeven in approximately November 1990 in greenhouses in Albany, Oreg. The mutation was discovered while taking cuttings of the parent cultivar, when one branch or one plant displayed variegated foliage, as opposed to the solid green foliage of the parent cultivar Rosebud TM Purple. The branch cutting was removed, planted, and grown out, with the variegation and foliage being commonly displayed throughout the plant. Subsequent asexual reproduction by stem cuttings taken by the inventor in Albany, Oreg., has shown that the unique features of this new cultivar are stabilized and are reproduced true to type in successive propagations.

The following characteristics taken in combination distinguish the new cultivar Blackberry Ice from both its parent and other cultivated *Impatiens sultanii* of this type known and used in the floriculture industry:

1. Fully double, consistent blooms.

2. Even growing, well shaped, mounded plant habit. Reasonably good self-branching if propagated from a vegetative cutting.

3. Rooting time is approximately seven days to initiate roots at 70° F.; saleable cuttings are available in 21 days at 70° F.

4. Produces cuttings very well. The highest quality cuttings are produced by removing from approximately 3" and leaf cuttings a ¼"-½" tip and discarding it. The remaining cutting then branches much better.

5. The foliage is normally green in the center surrounded by distinct white edges. At times when it is newly potted and growing extremely rapidly the white margin will become thinner and the green center will have a silver sheen over it.

6. The plant flowers in approximately six weeks from a pinched rooted cutting.

7. When left to reach full bloom, the plant is covered with blossoms which are red-purple in color.

8. Blackberry Ice has clear leaf variegation. The variegation varies in extent, but does not show signs of yellowing as leaves mature, as do some sports.

The new cultivar is similar in many respects to the parent cultivar Rosebud TM Purple, including similar red-purple flower color. The primary differences are in the leaf variegation of Blackberry Ice, and a more dense growth habit. The leaf color of the parent is essentially the same as the green base color of the leaves of the new cultivar.

The new cultivar can also be compared with the cultivar Peach Ice, a mutation of the cultivar Rosebud TM Salmon and disclosed in a pending plant patent application of Douglas S. Cole. Both cultivars are generally similar in variegation and growth habit, but the flower color of Peach Ice is generally coral and the base foliage color is a somewhat lighter green.

The accompanying colored photographs illustrate the overall appearance of the new cultivar, showing the colors as true as it is reasonably possible to obtain in a colored reproduction of this type. The top photograph is a front view of a fully grown plant of Blackberry Ice. The bottom photograph is a closeup view showing several flowers and variegated foliage.

The following is a detailed description of my new Impatiens cultivar based on plants produced under commercial practice at Albany, Oreg., and Loudon, N.H. Color references are made to The Royal Horticultural Society Colour Chart except where general terms of ordinary dictionary significance are used. The color values were determined during sunny conditions at approximately 1:00 p.m. under part natural and part inflorescent light in Alexandria, Va.

Parentage: Mutation of *Impatiens sultanii,* c.v. Rosebud TM Purple.

Propagation:

A. *Type cuttings.*—Stem and leaves, with the tip preferably being removed to enhance branching.

B. *Time to initiate roots.*—7 days at 21° C. summer; 7 days at 21° C. winter.

C. *Rooting habit.*—Good; roots at nodes or internodes; no hormones needed.

Plant Description:

A. *Form.*—Mounded form, with some spreading and slight hanging when given space.

B. *Habit of growth.*—Slower, denser growth than its green leaved parent; growth is comparable to other variegated cultivars and slower than comparable non-variegated cultivars; typical size plant grown in pot in spring programs is approximately 5–6" tall and 6–7" in diameter eight (8) weeks after planting, based on pinched, well-rooted 2" cutting.

C. *Foliage.*—The foliage color is comprised of three colors or shades: green, green with a silver sheen, and a white margin which varies in width, all in varying percentages.

1. Size (mature leaf):
   Width: 1" to 1¼".
   Length: 1¼ to 2" (excluding petiole).
2. Ovate, tip acuminate.
3. Texture: Smooth with some wrinkling.
4. Margin: Slightly serrated.
5. Color: Top side 137A-B overlaid with shiny white-grey on surface to provide a grey-green overall effect that is somewhat darker (more green) than 191A and not provided for on the R.H.S. Colour Chart; on immature foliage, edge variegation of 11C-D, which expands inwardly towards midrib in varying degrees as foliage matures. The underside is 138B-C, with same variegation. The differences in variegation patterns are clearly visible in the photographs and provide a very attractive appearance.
6. Venation: Not distinctive.

Flowering Description:

A. *Flowering habits.*—Flowers start as a bud the shape of a round ball and the size of a pea, and open similar to a rose in fullness. The flowers open slightly above or even with the foliage. Flowering is comparable to other cultivars, flowering in 5–7 weeks after potting a pinched, well-rooted 2" cutting.

B. *Flowering season.*—Year-round in greenhouse environment; best in spring.

C. *Flower buds.*—Basically white with a slight touch of green; red-purple color comes out as soon as bud cracks open; there are up to 5 buds per axil, usually 3, with the terminal bud opening first.

D. *Quantity of flowers.*—Excellent flower producer.

E. *Petals.*—Overall inflorescence has an almost rose or camellia type character due to fully double form.

1. Shape: Petals round to slightly oblong with indentation in tip.
2. Color: Upper surface: 74A, with a darker center eye between 72A and 74A; although color retention is good, there is some fading at maturity to 74B-C. Lower surface: 74C-74D.
3. Number of petals: Multiple, twenty-five or even more.
4. Size of flowers: 1¼" to 2".

F. *Reproductive Organs.*—

1. Stamens: Multiple in number; pollen color yellow.
2. Pistils: Stigma color yellow; styles and ovaries not distinctive.

G. *Fragrance.*—None.

H. *Spur.*—One per flower; attached near base, approximately 15 mm in length and curved; color varies from a generally transparent light green (no corresponding color value) to light purple, lighter than 78D, when flower is fully mature.

Disease Resistance: Some resistance to Botrytis. Root fungi are seldom a problem.

I claim:

1. A new and distinct cultivar of *Impatiens sultanii* plant named Blackberry Ice, as illustrated and described.

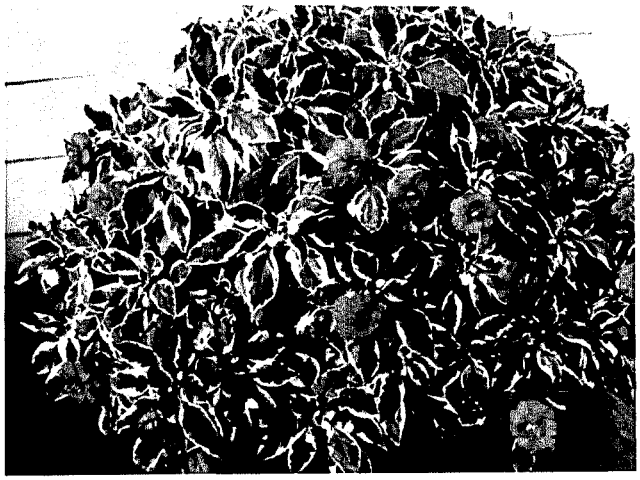
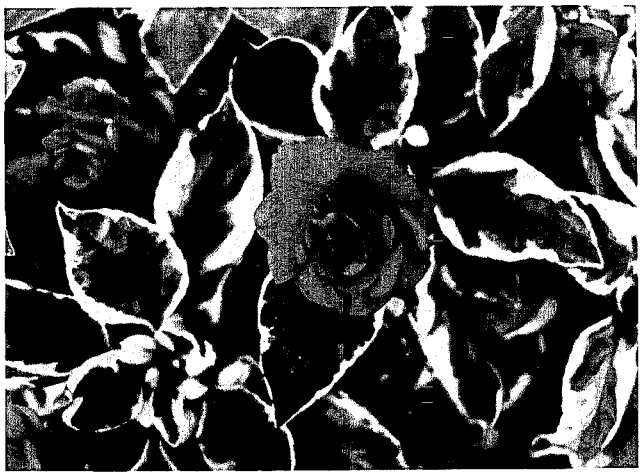

* * * * *